United States Patent [19]
Barreras, Sr. et al.

[11] Patent Number: 5,733,313
[45] Date of Patent: Mar. 31, 1998

[54] RF COUPLED, IMPLANTABLE MEDICAL DEVICE WITH RECHARGEABLE BACK-UP POWER SOURCE

[75] Inventors: Francisco Jose Barreras, Sr., Miami; Oscar Jimenez, Coral Gables, both of Fla.

[73] Assignee: Exonix Corporation, Miami, Fla.

[21] Appl. No.: 690,968

[22] Filed: Aug. 1, 1996

[51] Int. Cl.[6] .................................................. A61N 1/08
[52] U.S. Cl. ........................... 607/33; 607/60; 607/61; 128/903
[58] Field of Search ............................. 607/29–34, 60, 607/61; 128/903

[56] References Cited

U.S. PATENT DOCUMENTS

| | | |
|---|---|---|
| 3,942,535 | 3/1976 | Schulman . |
| 4,041,955 | 8/1977 | Kelly et al. . |
| 4,408,607 | 10/1983 | Maurer ........................ 128/419 R |
| 4,441,498 | 4/1984 | Nordling . |
| 4,793,353 | 12/1988 | Borkan ........................ 128/421 |
| 5,279,292 | 1/1994 | Baumann et al. ........................ 607/137 |
| 5,314,453 | 5/1994 | Jeutter ........................ 607/61 |
| 5,314,457 | 5/1994 | Jeutter et al. . |
| 5,476,488 | 12/1995 | Morgan et al. ........................ 607/32 |
| 5,480,415 | 1/1996 | Cox et al. ........................ 607/32 |

*Primary Examiner*—William E. Kamm
*Assistant Examiner*—Kennedy J. Schaetzle
*Attorney, Agent, or Firm*—Thomas R. Vigil

[57] ABSTRACT

The implantable, electrically operated medical device system comprises an implanted radio frequency (RF) receiving unit (receiver) incorporating a back-up rechargeable power supply and an implanted, electrically operated device, and an external RF transmitting unit (transmitter). RF energy is transmitted by the transmitter and is coupled into the receiver which is used to power the implanted medical device and/or recharge the back-up power supply. The back-up power supply within the receiver has enough capacity to be able to, by itself, power the implanted device coupled to the receiver for at least 24 hours during continual delivery of medical therapy. The receiver is surgically implanted within the patient and the transmitter is worn externally by the patient. The transmitter can be powered by either a rechargeable or non-rechargeable battery. In a first mode of operation, the transmitter will supply power, via RF coupled energy, to operate the receiver and simultaneously recharge the back-up power supply. In a second mode of operation, the receiver can, automatically or upon external command from the transmitter, acquire its supply of power exclusively from the back-up power supply. Yet, in a third mode of operation, the receiver can, automatically or upon command from the transmitter, alternatively acquire its supply of power from either, RF energy coupled into the receiver or the internal back-up power supply.

28 Claims, 6 Drawing Sheets

RF COUPLED, IMPLANTABLE MEDICAL DEVICE WITH RECHARGEABLE BACK-UP POWER SOURCE

BACKGROUND OF THE INVENTION

1. Field of the Invention

The present invention relates to an implantable medical device including a rechargeable back-up power source and a charging unit for recharging the back-up power source via RF coupling.

2. Description of the Related Art Including Information Disclosed Under 37 CFR §§1.97–1.99

The concept of using an implantable, electrically operated medical device for treating specific diseases or physical disorders is well known. Examples of implantable, electrically operated medical devices are: cardiac pacemakers which restore a sick human heart to a normal rhythm, neural simulators which control nerve or brain response (such as pain or epileptic seizures), infusion pumps for subcutaneously drug delivery (such as insulin pump), and diagnostic devices for monitoring a patient's condition.

With respect to all of these implantable, electrically operated devices, it is necessary to provide power to the device implanted below the skin. Since the medical device is subcutaneously implanted in the patient, the power source must supply electrical energy for a reasonable period of time in order to reduce further surgical trauma to the patient and financial cost to the medical provider.

Implantable, electrically operated medical devices can be classified in three general areas: radio frequency (RF) coupled and partially powered implanted devices, non-rechargeable battery powered totally implanted devices, and devices which combine RF coupling and battery powered systems.

The RF coupled and powered devices do not carry or contain an independent power source. Therefore, the RF coupled device requires an external RF transmitter and a surgically implanted receiver. Such a device is an RF coupled neural stimulator. The RF link transfers stimulation pulses percutaneously through the skin and adjacent tissue layers of the patient from the external RF transmitter to the surgically implanted RF receiver and stimulator device. The transmitter sends, on a real-time basis, stimulation pulses to be applied ultimately to the implanted electrodes plus programming data defining the polarity of each electrode relative to each other to the implanted stimulation device. The implanted receiver obtains these stimulation pulses and programming data, converts pulses as necessary, delivers the energy contained in each transmitted stimulation pulse to the implanted electrodes as defined in the real-time programming data. The stimulation energy for each stimulation pulse is inductively coupled on a real-time basis from the external transmitter to the implanted receiver.

The common disadvantage of the RF coupled and powered stimulator is that the patient must always wear the external transmitter and antenna (even during sleep) in order for the implanted receiver to deliver stimulation pulses to the targeted tissue. Stimulation therapy ceases the moment the transmitter antenna is withdrawn just a few inches away from the implanted receiver. Although the RF coupled stimulator has this disadvantage, the service life of such an RF coupled and powered stimulator is not limited to the life of a battery contained within a fully implantable stimulation unit. Accordingly, the long term cost of the RF coupled and powered simulators is less than the non-rechargeable battery powered simulators because the service life of the former is much longer than that of the latter. RF coupled and powered simulators have been commercially marketed by Medtronic of Minneapolis, Avery Laboratories of New York and Neuromed of Dallas, Tex.

The battery powered stimulator utilizes a primary, non-rechargeable battery to power the implanted stimulator. The battery provides sole and exclusive power to the implanted stimulator continually while the stimulator generates one or more electric stimulation pulses, in a controlled manner, to the targeted tissue. Of course, the stimulation pulses are delivered to the targeted tissue via implanted leads. An external programmer may be used to non-invasively adjust the stimulation parameters, such as amplitude, pulse width or rate, or to control the duration of stimulation therapy each day. Programming may be provided through an RF telemetry link. After programming, the stimulator remembers the parameter values (the values are stored in an electronic memory) as long as the battery voltage remains above a minimum voltage level required by the electronics. Unfortunately, the service life of these battery powered implantable simulators is limited to the battery life. Accordingly, it is necessary to surgically remove and then replace the battery powered implantable simulators upon depletion of the electrochemically active materials in the battery. This disadvantage (i.e. surgical replacement) increases its long term cost to the medical provider relative to the aforementioned RF coupled and powered simulators. The battery powered implantable simulators do not require an external transmitter to deliver the stimulating electrical pulses. Accordingly, the battery powered implantable simulators are less complicated to use and more comfortable to wear than the RF coupled and powered simulators. Battery powered simulators have been marketed by Medtronic of Minneapolis and Exonix of Miami.

A third category of implantable, electrically operated devices include neural simulators which combine the RF coupled/powered systems with the battery powered implantable stimulator technology. These types of simulators enable the patient to obtain therapy without the necessity of having an external RF coupled unit proximate to the implant at all times. However, the stimulator must be surgically replaced after the battery is depleted if use of the external RF transmitter is not desired. This type of stimulator allows RF coupled stimulation at times when wearing the external transmitter is not objectionable, thereby extending battery life. Also, this type of stimulator may allow for continuing RF coupled stimulation after the internal power source is depleted, although some of these RF coupled and battery powered implantable simulators do not operate if the battery is completely depleted in the implanted stimulator.

Several examples of such previously proposed implantable devices are disclosed in the following U.S. patents:

| U.S. Pat. No. | Patentee |
| --- | --- |
| 4,408,607 | Maurer |
| 4,793,353 | Borkan |
| 5,279,292 | Baumann et al. |
| 5,314,453 | Jeutter |

U.S. Pat. No. 5,314,453 to Jeutter describes and claims an implant "locator" means to aid in locating an implanted device. The locator means comprises a reed switch affixed to the center of a transmitting coil and a magnet affixed within the implanted device. Transmission of high frequency RF energy is possible only when the reed switch is closed by the magnet within the implanted device, thus insuring some degree of good coupling between the transmitter and receiver. However, this patent describes a full wave rectifier along with rechargeable batteries. Accordingly, it incorporates a rechargeable battery. The present invention differs from the teachings of the Jeutter patent in the following respects:

1) Charging current is controlled by battery temperature to prevent gas generation by the battery and loss of battery electrolyte,
2) A real-time feedback system is provided between the receiver and the transmitter for real-time adjustment of the RF energy generated by the transmitter, thereby extending the service time of the transmitter's battery.
3) A low frequency RF coupling method (10 to 500,000 Hertz) is provided which allows RF coupling through a titanium encased receiver. The RF coupling system described by Jeutter operates at a very high frequency of 2,000,000 Hertz which is greatly attenuated by any metal enclosure. Jeutter describe an epoxy potted receiver which differs from a titanium encased receiver housing.
4) The receiver is capable of automatic switching the supply of power between RF coupled power upon sensing RF energy or battery power upon sensing loss of RF coupled power.

U.S. Pat. No. 5,279,292 to Joachim Baumann et al. teaches a series resonant circuit in an implantable device. The device disclosed hereinafter uses a parallel resonant circuit which can be tuned at low frequencies, 60 Hz to 500 kHz, such as, for example 8 kHz, which couples well through a titanium enclosure. Further this patent does not teach adjusting charging current as a function of battery temperature or controlling the charging current with the current output from a D/A converter.

U.S. Pat. No. 4,793,353 to William Borkan discloses a non-invasive multiprogramable tissue stimulator which utilizes RF coupling to charge and recharge a capacitor or other rechargeable voltage source. The Borkan circuit differs from the circuit disclosed hereinafter in several respects:

1) First of al in the Borkan circuit, while in the RF stimulation mode, each stimulation pulse must be generated and transmitted by the transmitter, on a real time basis, to the implanted receiver (in contrast, the receiver disclosed hereinafter incorporates all the elements required to autonomously generate and regulate the stimulation pulses);
2) Borkan teaches that a non-rechargeable battery can be used as an alternative power source to RF coupled stimulation, while the circuit disclosed hereinafter uses a rechargeable battery which can be "fast" or "trickle" recharged via low to medium frequency (10 to 500,000 Hertz) RF coupling while Borkan uses a much higher RF coupling (2,000,000 Hertz).

U.S. Pat. No. 4,408,607 to Donald Maurer teaches a capacitive energy source and associated circuitry for powering a medical apparatus. The Maurer circuitry differs from our the circuitry disclosed hereinafter in that:

1) The Maurer battery is non-rechargeable and only is used to power the implanted receiver during charging of the capacitor (the main power source);
2) Maurer provides no means for non-invasively recharging the battery;
3) Maurer does not control the charging current to a battery relative to the temperature of the battery to prevent gas generation by the battery and loss of battery electrolyte.

Moreover, Maurer does not teach the capability to switch automatically between RF coupled (power upon detection of RF energy) and battery power (upon sensing absence of RF energy).

SUMMARY OF THE INVENTION

According to the present invention there is provided an implantable, electrically operated medical device comprising an implanted radio frequency (RF) receiver incorporating a rechargeable back-up power source and an external RF transmitter. RF transmissions are coupled into the implanted receiver for powering delivery of medical therapy and simultaneous recharging of the back-up power source within the receiver. The back-up power source has enough capacity to be able to autonomously power the receiver for at least seven days during continual delivery of medical therapy. The receiver is surgically implanted within the patient and the transmitter is worn externally by the patient. The transmitter can be powered by either a rechargeable or non-rechargeable battery.

In a first mode of operation, the supply of power to operate the receiver, recharge the back-up power source and deliver therapy is acquired primarily from the RF energy coupled into the receiver, until the receiver senses a loss of RF power at which point it will automatically switch to the back-up power source in order to continue delivery of medical therapy. In this first mode of operation, the transmitter will transmit lower energy RF waves since the back-up power source is recharged at a slower rate.

In a second mode of operation, the receiver can, automatically or upon external command from the transmitter, acquire its supply of power exclusively from the back-up power source. In the second mode of operation, the transmitter will transmit high energy RF waves in order to recharge the back-up power source at a faster rate and will terminate the RF transmission upon receiving from the receiver a "termination command" which indicates that the back-up power source is fully charged.

Yet, in a third mode of operation, the receiver can, automatically or upon command from the transmitter, alternatively acquire its supply of power from either or both, RF energy coupled into the receiver and/or the internal back-up power source. This third mode of operation is useful in patients where it is desirable to power the receiver from RF coupled energy during periods of awakeness, but switch to the back-up power source during sleep for greater comfort. In this third mode of operation, a real time clock within the receiver can be programmed by the transmitter with different start/stop times for RF coupled power than for back-up battery power. In this fashion, the switching is done automatically and the external transmitter unit will alert the patient which is the source of power for the receiver at all times.

The receiver includes a mechanism for alerting the patient when the back-up power source is nearing depletion and needs to be recharged. The mechanism can include: 1) a vibrating device within the receiver; 2) an audible tone generating device within the receiver; or, 3) a specific message shown in the transmitter's display combined with a specific audible tone generated by the transmitter.

The transmitter incorporates a transmitting antenna which generates RF wave-fronts which are coupled into an inductor within the implanted receiver. This RF coupled power, which is alternating current or AC in nature, is rectified, filtered and converted into a high DC voltage within the receiver. Further, a voltage regulator within the receiver converts the high DC voltage into a lower precise DC voltage from which the receiver operates.

It is the objective of the present invention to provide an implantable, electrically operated medical device (receiver) capable of obtaining its source of electrical power from either, an external battery coupled via low level RF transmissions (transmitter), or a back-up rechargeable battery contained within the implanted receiver.

According to one aspect of the present invention, there is provided a method of supplying power, on an exclusive basis, from externally low energy RF coupled power (transmitter), to an implanted receiver during continual delivery of medical therapy.

According to another aspect of the present invention, there is provided circuitry for programming into the receiver the times of day (meaning a continuous 24 hour period) in which the receiver automatically switches it's supply of power from RF coupled energy to the back-up power source, and vice-versa.

According to still another aspect of the present invention, there is provided a method for recording into a non-volatile memory contained within the implanted receiver the stimulation values and other critical data, so that it will not be erased if the back-up power source is depleted and to eliminate the need for the transmitter to generate and regulate, on a real time basis, the delivery of medical therapy.

According to still another aspect of the present invention, there is provided a method of supplying power, on an exclusive basis, during at least a seven day cycle of substantially continual delivery of medical therapy utilizing a rechargeable power source.

According to still another aspect of the present invention, there is provided a method for non-invasively recharging the power source within the receiver, whereby the electrical energy contained in the battery powering the external transmitter is transferred into the rechargeable power source within the receiver utilizing an inductive RF power link between the external transmitter (recharging unit) and the implanted receiver (unit being recharged).

According to still another aspect of the present invention, there is provided a method for regulating the rate of recharging the back-up power source contained within the implanted receiver as a function of temperature of the back-up power source, in order to inhibit the power source from generating harmful gases and to prevent electrolyte loss, thereby enhancing the service life of the back-up power source and increasing the possible number of recharge cycles.

According to still another aspect of the present invention, there is provided a method, interactive between the transmitter and receiver, for regulating the RF energy generated by the external RF transmitter as a function of distance between the transmitting and receiving inductors.

With these methods, the level of RF energy coupled into the receiver antenna is monitored by the receiver which telemeters specific commands to the RF transmitter to adjust the RF energy level being generated. This real-time feedback system allows generation of just the minimum RF power needed at the receiver, thereby extending the service time of the battery powering the RF transmitter.

According to still another aspect of the present invention, there is provided in transmitter for the patient to select between RF powered operation only, back-up power source operation only, or a combination of both. If "RF power" is selected, the implanted receiver will only operate when the transmitter unit is proximate to the implanted receiver, and the transmitter will generate low level RF energy. If "back-up power" is selected, the implanted receiver will draw it's operating power exclusively from the back-up power source, and the transmitter will generate higher level RF energy when used to quickly recharge the back-up power source. If "combination power" is selected, the implanted receiver will draw it's operating power from the transmitter via low level RF coupled energy, but will automatically switch to draw it's operating power from the internal back-up power source when the transmitter is removed or turned off. The patient may select one of these options via a specific menu shown in the transmitter's display.

According to still another aspect of the present invention, there is provided a method for the receiver to automatically terminate the recharge cycle upon sensing a fully charged back-up battery by the transmission of a specific telemetry command to the transmitter, thereby enhancing the service life of the battery powering the RF transmitter.

According to still another aspect of the present invention, there is provided several receiver-initiated commands for alerting the patient when the rechargeable power source is nearing depletion and needs to be recharged. Some alerting signals are generated by the receiver itself and other alerting signals are generated by the transmitter.

According to still another aspect of the present invention, power sources and methods are utilized for non-invasively coupling energy and recharging the implanted battery, in combination with an implantable tissue stimulator.

According to still another aspect of the present invention, there is provided an implantable drug delivery system utilizing these power sources and methods for non-invasively coupling electric energy into the implanted drug delivery system and recharging its battery.

According to still another aspect of the present invention, there is provided an implantable monitor and diagnostic system utilizing these power sources and methods for non-invasively coupling electrical energy into the implanted monitor which is used to collect vital physical data from the patient which can be interrogated by a receiver external to the patient.

According to still another aspect of the present invention, there is provided an implantable cardiac pacemaker utilizing these power sources and methods for non-invasively coupling electrical energy into the implanted pacemaker and recharging its battery.

According to still another aspect of the present invention, there is provided an implantable cardioverter/defibrillator utilizing these power sources and methods for non-invasively coupling electrical energy into the implanted cardioverter/defibrillator and recharging its battery.

According to still another aspect of the present invention, there is provided a method for recharging power via an inductive RF power link between the recharging unit and the implant and through the hermetic titanium encasement of the implant.

According to still another aspect of the present invention, a patient is permitted to vary the delivery schedule and/or quantities of the medical therapy via the external RF transmitter/recharger unit.

According to still another aspect of the present invention, a medical physician, nurse or technician is allowed to program into the implanted medical device, via the external RF transmitter/recharger unit, the delivery schedule, values or quantities of the medical therapy and to set the limit for these schedules, values or quantities within which the patient may safely adjust them later on.

DESCRIPTION OF THE PREFERRED EMBODIMENT(S)

Figure 1:
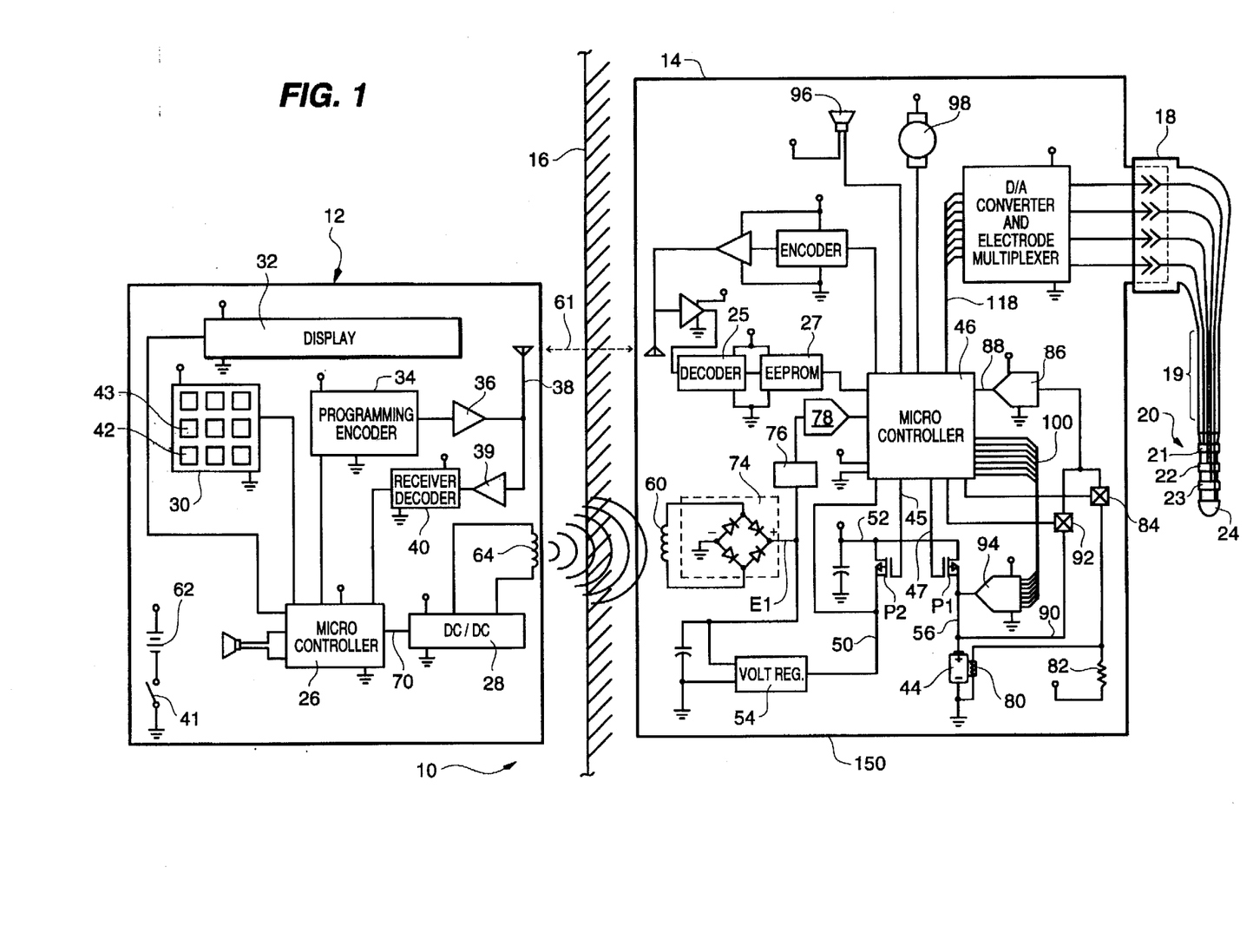
FIG. 1 is a block electrical, schematic circuit diagram of the overall system including a transmitting unit and an implanted receiver unit configured for an implantable, rechargeable tissue stimulator system.

Referring to the drawings in greater detail, there is illustrated in FIG. 1 a block electrical schematic circuit diagram of an implantable, rechargeable tissue stimulator system 10. The system 10 includes a transmitter 12 and a receiver 14, the latter being surgically implanted beneath a patient's skin 16. The receiver 14 is connected, via lead connector 18, to an implanted medical device, which in this embodiment, is an implanted lead 19 which contains, at it's distal end 20, stimulating electrodes 21–24. These electrodes 21–24 are implanted adjacent to the target tissue to be stimulated (i.e., a specific nerve or a nerve bundle, a specific area of the brain or a specific muscle within the human body). The implanted receiver 14 receives therapy values, transmitted by the transmitter 12 via RF signals, which are decoded by decoder 25 and then stored in a non-volatile memory (EPROM) 27.

Referring again to FIG. 1, the major components of the transmitter 12 are a micro controller 26 which is used, via software, to: 1) control the output of a programmable DC to DC converter 28 in order to regulate the amount of RF energy to be coupled into the receiver 14; 2) read data and command inputs inputted via a keyboard 30, display messages and menus via a display 32, transmit therapy parameter values, via a programming encoder 34, a transmit driver 36 and an antenna 38, to the implanted receiver 14; 3) and receive commands and patient's diagnostic data, transmitted from the implanted receiver 14, via the antenna 38, an amplifier 39 and a decoder 40.

As shown in FIG. 1, when the transmitter 12 is powered up via a switch 41 and a "start therapy" key 42 on the keyboard 30 is pressed, the transmitter 12 will transmit the "start" command to the receiver 14 which will initiate delivery of therapy by the receiver 14. Likewise, if a "stop therapy" key 43 on the keyboard 30 is pressed, the transmitter 12 will transmit the "stop" command to the receiver 14 which will cease delivery of therapy.

The implanted receiver 14 of FIG. 1 can be programmed by the physician or patient to obtain it's operating power from one of three sources: 1) RF coupled energy only; 2) back-up rechargeable power supply/source 44 only; or 3) a combination of both whereby the implanted receiver 14 alternates automatically from one to the other according to a preset schedule programmed via the transmitter 12.

When "RF only" is selected from a menu displayed by the display 32 of the transmitter 12, an output port 45 of a micro controller 46 in the receiver 14 is switched to a "0" and a port 47 is switched to a "1" which places pmos transistor P2 in a conducting state and pmos transistor P1 in a non-conducting state. This effectively connects a line conductor 50 to a line conductor 52, making VDD equal to the output of a voltage regulator 54 which is at +3.0 vdc.

When "battery only" is selected from the same menu, the output port 47 is switched to a "0" and the port 45 is switched to a "1", thus effectively connecting line conductor 56 to line conductor 52 and making VDD equal to the voltage level at the rechargeable power source 44.

As shown in FIG. 1, when "combination" is selected from the same menu, the system 10 will automatically switch the source of VDD to the output of the voltage regulator 54 (line conductor 50) when the transmitter 12 is proximal to the receiver 14, or to the rechargeable power source 44 when the transmitter 12 is removed away from the receiver 14. The automatic switching is performed by the micro controller 46 in response to the state of line conductor 50 which is at +3.0 volts when RF energy is being coupled into an inductor 60 (the transmitter 12 is proximal to the receiver 14) or is 0 volts in the absence of RF energy (the transmitter 12 is away from the receiver 14).

When the receiver 14 is programmed to "battery only" power acquisition mode, it's exclusive source of operating power becomes the rechargeable power source 44. After prolonged use, the rechargeable power source 44 will reach a near depleted level, at which point the receiver 14 will transmit, via an RF communication link 61, a "recharge" command to the transmitter 12. This will cause the transmitter 12 to generate, via the battery 62, the DC/DC converter 28 and an output inductor 64, high energy RF waves which are coupled into the inductor 60 contained within the receiver 14. The actual level of RF energy generated by the inductor 64 is regulated by an output port 70 of the micro controller 26 as a real-time response to data transmitted by the receiver 14 via the micro controller 46, the data representing the voltage level E1 at the output of the rectifier 74 in the receiver 14 which is measured via an attenuator 76 and an analog to digital converter 78. This feedback system extends the life of the battery 62 within the transmitter 12, by adjusting, as a function of distance between the inductors 64 and 60, the RF energy required to quickly recharge the rechargeable power source 44. A close proximity requires much less RF energy to recharge the rechargeable power source 44 than a longer distance would, in the same time. During this recharging operation, the micro controller regulates, as a function of temperature, the current level used to recharge the rechargeable power source 44. The temperature is measured by a thermistor 80 which is adhered to the rechargeable power source 44 during manufacturing. The junction between the thermistor 80 and a resistor 82 form a voltage divider which is fed through an analog switch 84 to an analog to digital converter 86 and, via a line conductor 88, to the micro controller 46. As the voltage rises, the ohmic value of the thermistor 80 drops proportionally to the temperature, thus reducing the voltage at the line conductor 88 to the micro controller 46. This loop forms a temperature-controlled, current-regulated charging system which restricts the temperature rise of the rechargeable power source 44 during recharging, thus preventing the power source 44 from suffering electrolyte starvation and gas generation. Both of these phenomena will, if left unchecked, dramatically reduce the reliability and service life of the power source 44. Also, during recharging of the power source 44, the micro controller 46 will monitor the voltage level of the power source 44 via a line conductor 90, analog switch 92, the A/D converter 86 and, finally, the line conductor 88. Upon sensing a fully charged state, the micro controller 46 will telemeter to transmitter 12, via the RF communications link 61, a "stop" recharging command and simultaneously will turn off a D/A converter 94 which will cut off the current needed to charge the rechargeable power source 44. In this manner, the power source 44 cannot be overcharged, even if the "stop" command was not received by the transmitter 12 due to electromagnetic interference.

Referring to FIG. 1, when the receiver 14 is programmed to "RF only", the power acquisition mode, it's exclusive source of operating power is the low level RF energy generated by transmitter 12 and coupled into the inductor 60 within the receiver 14. The actual level of RF energy generated by the inductor 64 is regulated by the output port 70 of the micro controller 26 to the minimum level required to operate the receiver 14 and the rechargeable power source 44 is trickle charged, as a real-time response to data transmitted by the receiver 14 via the micro controller 26, i.e., the data representing the voltage level E1 at the output of the rectifier 74 which is measured via the attenuator 76 and the analog to digital converter 78. This feedback system extends the life of the battery 62 within the transmitter 12, by adjusting the RF energy required to operate the receiver 14 and maintain a trickle charge to the rechargeable power source 44, as a function of the distance between the inductors 64 and 60. At close proximity, much less RF energy is required to accomplish these functions than at a longer distance.

During trickle charging, the micro controller 46 regulates, as a function of temperature, the current level used to trickle charge the power source 46, by the same method already explained in the previous paragraph. Again, this prevents electrolyte starvation and gas generation within the rechargeable power source 44. Also, during trickle charging, the micro controller 46 will monitor the charge level of the power source 44, and upon sensing a fully charged state, the receiver 14 will telemeter to the transmitter 12 the "stop" recharging command and simultaneously will turn off the D/A converter 94 which will cut off the current needed to charge the power source 44. In this manner, the power source 44 cannot be overcharged, even if the "stop" command was not received by the transmitter 12 due to electromagnetic interference.

When the receiver 14 is programmed to "combination" power acquisition mode, the micro controller 46 will automatically switch delivery of operating power to the receiver 14 to RF coupled energy upon detection of RF induced voltage at E1. Likewise, the micro controller 46 will switch delivery of operating power to the rechargeable power source 44 upon loss of RF induced voltage at E1. The patient may select, via a menu shown in the transmitter's display 32, fast or trickle charge to the rechargeable power source Upon sensing that the charge in the rechargeable power source 44 is below a predetermined level, the micro controller 46 signals the patient, via an audible alarm 96 and/or a vibrating alarm 98, that the rechargeable power source should be recharged.

Figure 2A:
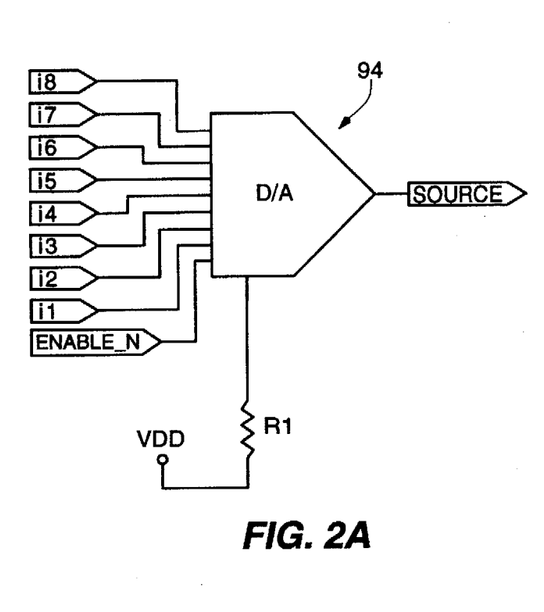
FIG. 2A is a block electrical schematic circuit of a digital to analog converter in the receiver unit
Figure 2B:
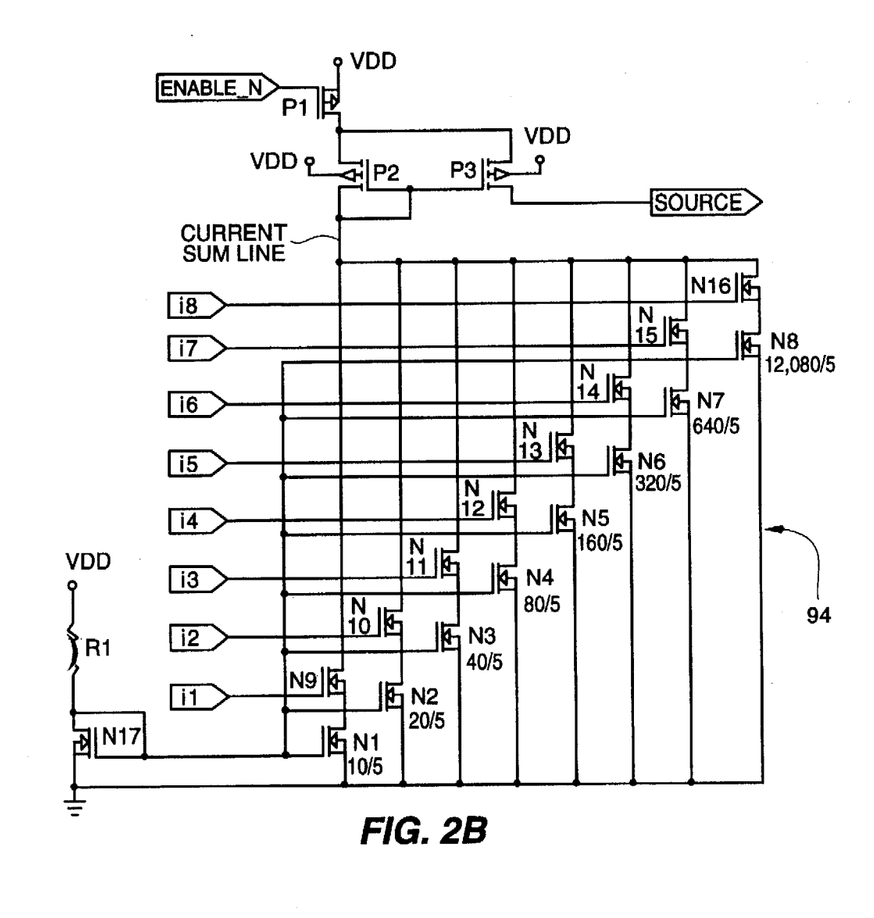
FIG. 2B is a detailed electrical schematic circuit diagram of the digital to analog converter with current output shown in FIG. 2A which is used, under control of a micro controller, to regulate the constant current rate for recharging the back-up power source within the implanted receiver unit.

Referring to FIG. 2B, a detailed electrical schematic of the digital to analog (D/A) converter 94 is provided. The D/A converter 94 is software programmable, precision current source whose output is regulated by the micro controller 46. It should be noted that this type of D/A converter is best implemented into an integrated circuit where the electrical characteristics of the transistors can be precisely matched.

Referring again to FIG. 2B, resistor R1 is used to set the base bias current for the converter 94. Transistors N17 and N1 form a 1:1 current mirror where the current into the transistor N17 equals the current through the transistor N1, since both transistors have equal channel width and length. However, the channel width for the transistors N2 through N8 are binary weighted, so that the transistor N2 has twice the width of the transistors N1, N3 has twice the width of N2, and so forth. This binary scaling results in transistor N2 conducting twice the current of transistor N1 (assuming equal bias current), the transistor N3 conducting twice the current of the transistor N2, and so forth. The transistors N9 through N16 are used as pass devices to allow the current available at the transistor N1 through the transistor N8 to pass to the current sum line 1. The on-off state for the transistors N9 through N16 is governed by inputs i1 through i8 which, in one embodiment, are output ports from the micro controller 46 (bus line 100 in FIG. 1). In this manner, the micro controller 46 is able to select any value of current between 1 and 256 times that of the current flowing through the resistor R1 (bias current) to pass to the current sum line 1.

Input line "enable.n" is used to turn on and off the D/A converter. When "enable.n" is a "0", the transistor P1 conducts connecting VDD to the sources of the transistors P2 and P3 which form a 1:1 current mirror. Therefore, the current sourced by the transistor P3 equals the current flowing through the transistors P2, P3 being the output current device ("iSOURCE") for this D/A converter 94.

Figure 3:
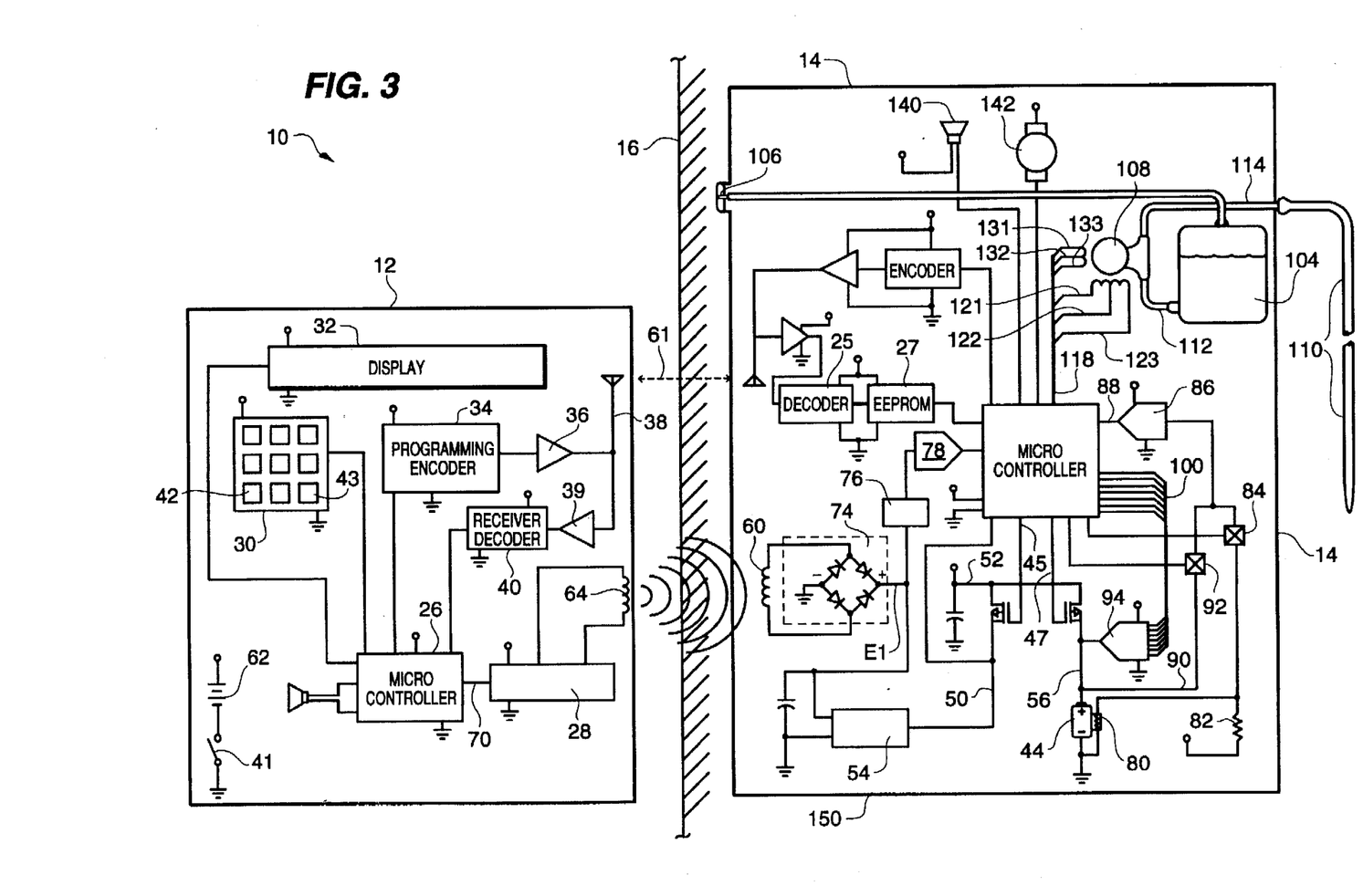
FIG. 3 is a block electrical schematic circuit diagram of the overall system as configured for an implantable, rechargeable drug delivery system.

In FIG. 3 is shown a block diagram for an implantable, rechargeable drug delivery system. The block diagram for the transmitter 12 is the same as for the transmitter 12 shown in FIG. 1.

The block diagram for the receiver 14 contains the same power supply system, supply switching means and method for recharging the rechargeable power source 44 that has been already described above in connection with the description of FIG. 1, but has been modified to incorporate the components required to assemble an implantable drug delivery system. These components are: 1) a drug reservoir 104 which contains the drug to be delivered by the receiver 14; 2) a refill septum 106 used to percutaneously, via a hypodermic needle, refill the drug reservoir 104; 3) a portioning pump 108 used to dispense a precise volume of drug to a catheter 110 by making one or more small injections (portions); 4) a pump inlet tube 112; 5) a pump outlet tube 114; 6) the drug delivery catheter 110 which is used to carry and deliver to the target tissue the drug volume dispensed by the pump 108; and 7) a multi-wire cable 118 which carries the electrical signals for driving the pump 108.

Referring again to FIG. 3, the wire conductors 121–123 are used to drive the pump 108 and the wire conductors 131–133 are used to sense when a portion has been delivered. The micro controller 46 measures the time required for delivering each drug portion, and based on this time determines if the pump 108 is empty or contains fluid, since the former condition results is a faster time than the latter. Upon sensing a "pump empty" condition, the micro controller 46 signals the patient, via an audible alarm 140 and/or a vibrating alarm 142, that the reservoir 104 is empty. It should be noted that the titanium housing 150 of the receiver 14 should be in close proximity to the audible alarm 140 in order to transmit the sound waves to outside the human body.

Figure 4:
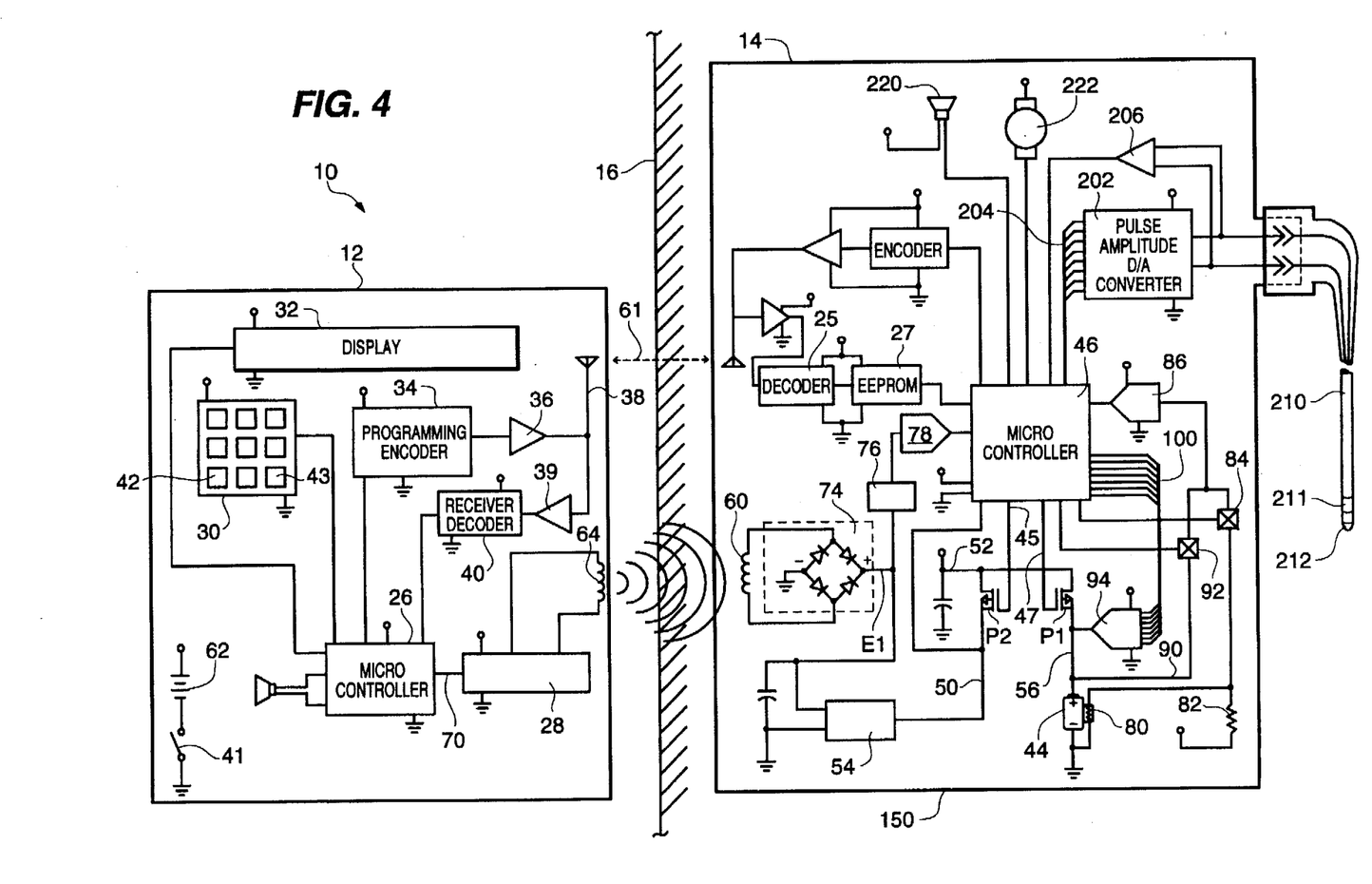
FIG. 4 is a block electrical schematic circuit diagram of the overall system as configured for an implantable, rechargeable cardiac pacemaker system.

FIG. 4 is a block diagram of an implantable, rechargeable cardiac pacemaker system. The block diagram for the transmitter 12 is the same as for the block diagram of the transmitter 12 shown in FIG. 1.

The block diagram for the receiver 14 contains the same power supply system, supply switching means and method for recharging the rechargeable power source 44 that already have been described above in connection with the description of FIG. 1, but has been modified to incorporate the components required to assemble an implantable, rechargeable cardiac pacemaker system. These components are: 1) a pulse amplitude D/A converter 202 which is used to regulate, under command of the micro controller 46, the amplitude of the stimulating pulses delivered to the human heart; 2) a bus 204 which carries the binary value for the amplitude from the micro controller 46 to the D/A converter 202; 3) an amplifier and filter 206 which detects and amplifies the cardiac depolarization waves (such as R or P waves) and filters out other signal frequencies not related to cardiac activity; 4) an implanted lead 210 containing electrodes 211–212 which is used to deliver stimulating pulses to the heart in order to regulate the heart's rhythm, but which is used also to pick-up and carry the cardiac depolarization waves to the amplifier/filter 206. These cardiac waves are used by the micro controller 46 to measure the intrinsic rate of the heart. The measurement is utilized to determine if electrical stimulation pulses are needed to speed-up the heart.

Upon sensing that the charge in the rechargeable power source 44 is below a predetermined level, the micro controller 46 signals the patient, via an audible alarm 220 and/or a vibrating alarm 222, that the rechargeable power source 44 should be recharged.

Figure 5:
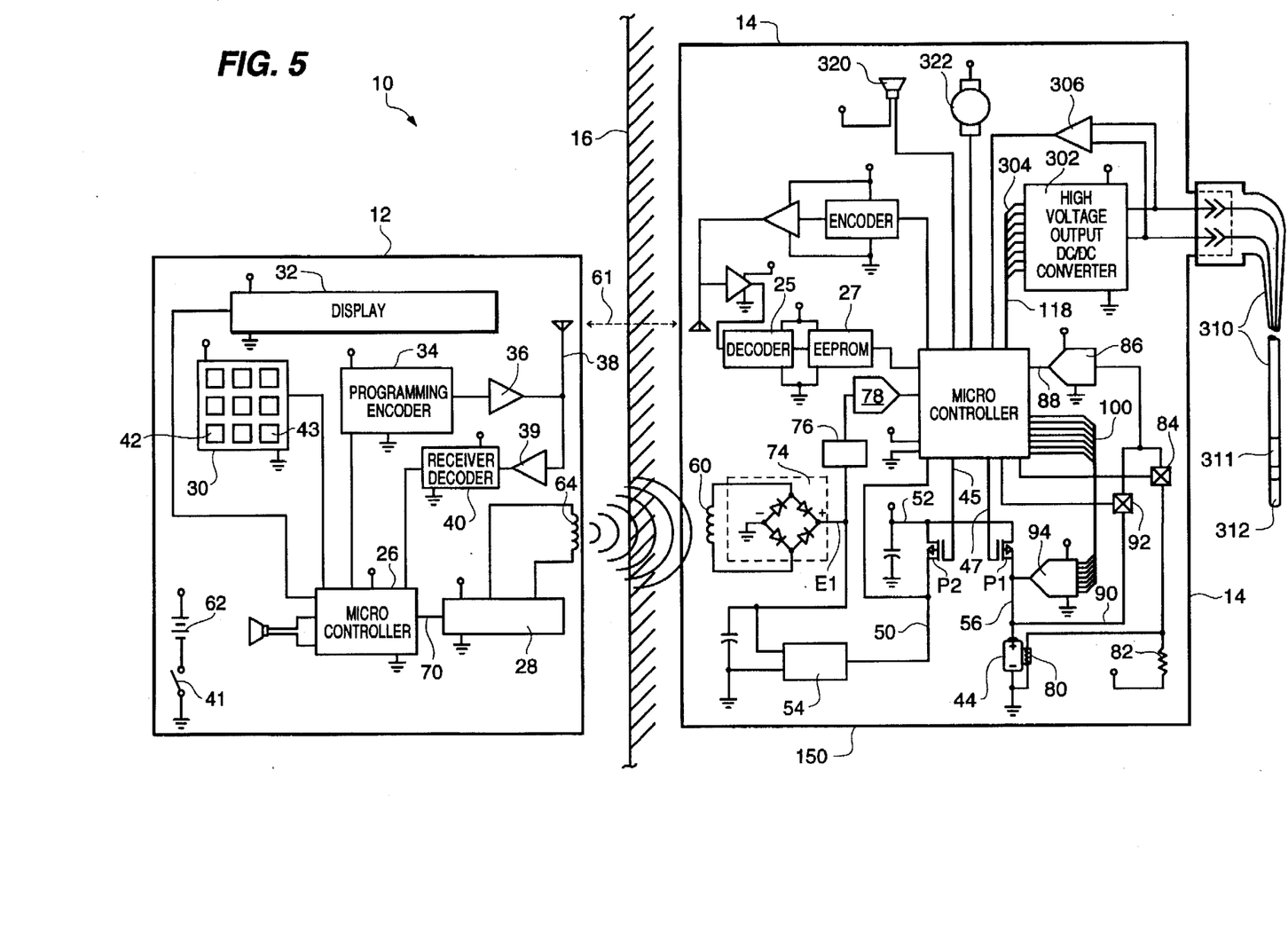
FIG. 5 is a block electrical schematic circuit diagram of the overall system as configured for an implantable, rechargeable cardioverter/defibrillator.

In FIG. 5 is illustrated a block diagram of an implantable, rechargeable cardioverter/defibrillator. The block diagram for the transmitter 12 is the same as the block diagram for the transmitter 12 shown in FIG. 1.

The block diagram for the receiver 14 contains the same power supply system, supply switching means and method for recharging the rechargeable power source 44 that already have been described above in connection with the description of FIG. 1, but has been modified to incorporate the components required to assemble an implantable, rechargeable cardioverter/defibrillator system. These components are: 1) a high voltage output, DC to DC converter 302 used to convert the low voltage available at the rechargeable power source 44 to a relatively higher voltage required to cardiovert a fibrillating human heart; 2) a bus 304 which carries the binary value for the voltage amplitude from the micro controller 46 to the D/A converter 302; 3) an amplifier/filter 306 used to detect the presence of a cardiac arrhythmia such as fibrillation or tachycardia; and, 4) an implanted cardioverting lead 310 containing cardioverting electrodes 311–312.

As shown in FIG. 5, the DC/DC converter 302 is used to generate either low voltage pulses to pace the human heart when needed or high voltage pulses to shock a large number of cardiac cells into synchrony, thereby restoring a normal cardiac rhythm. The micro controller 46, via the bus 304, regulates the timing and amplitude of low voltage pulses or high voltage shocks, depending if an arrhythmia is detected or not. Upon sensing that the charge in the rechargeable power source 44 is below a predetermined level, the micro controller 46 signals the patient, via an audible alarm 320 and/or a vibrating alarm 322, that the rechargeable power source 44 should be recharged.

Figure 6:
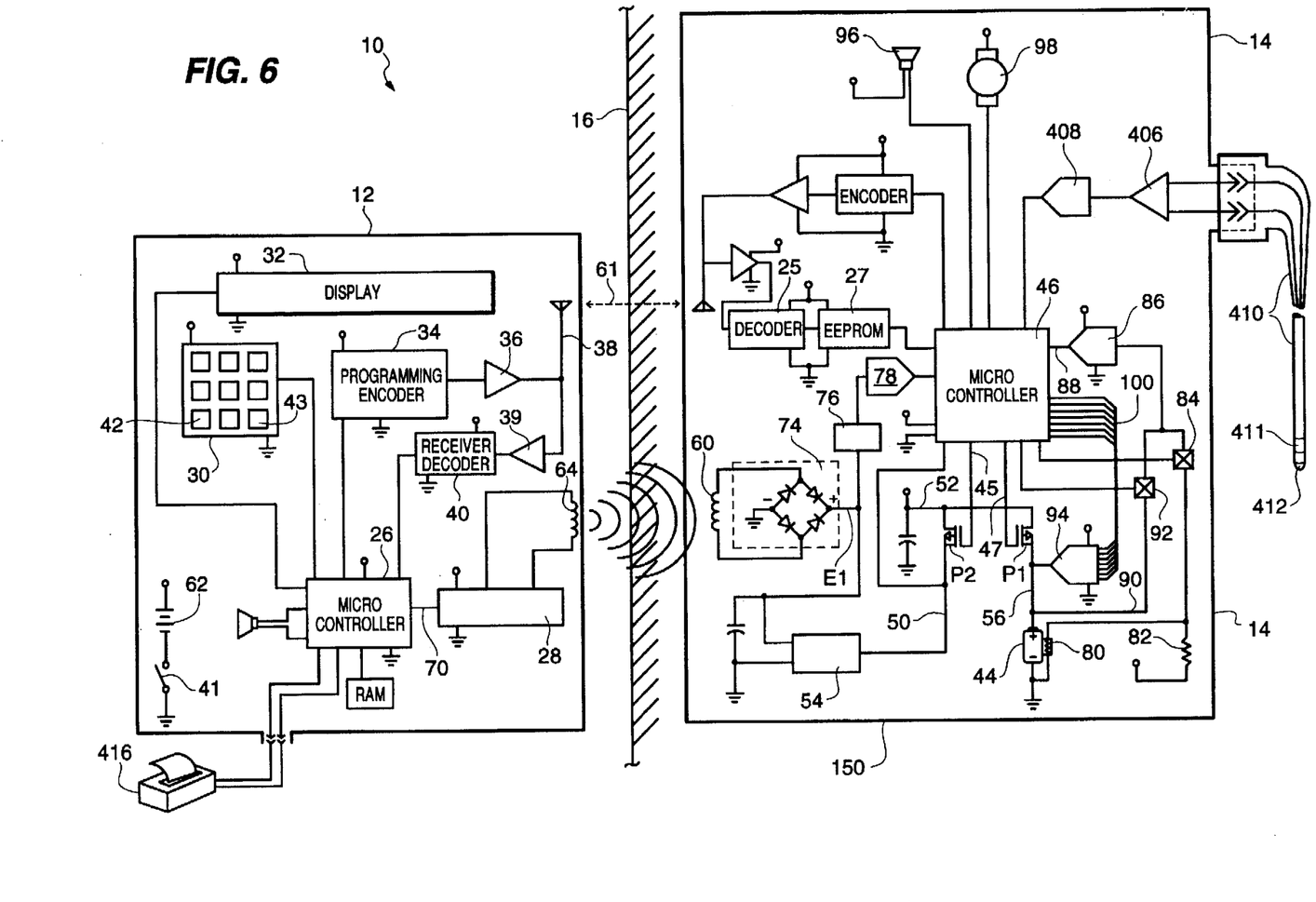
FIG. 6 is a block electrical schematic circuit diagram of the overall system as configured for an implantable, rechargeable monitor and diagnostic system.

In FIG. 6 there is illustrated a block diagram of an implantable, rechargeable monitor and diagnostic system. The block diagram for the transmitter 12 is the same as the block diagram for the transmitter 12 shown in FIG. 1.

The block diagram for the receiver 14 contains the same power supply system, supply switching means and method for recharging the rechargeable power source 44 that already have been described in connection with the description of FIG. 1, but has been modified to incorporate the components required to assemble an implantable, rechargeable monitor and diagnostic system. These components are: 1) an amplifier/filter 406 used to amplify the desired biological signals and to filter out other undesirable signals; 2) an analog to digital converter 408 which is used to convert the biological signal into a digital value representative of frequency and amplitude of the biological signal; 3) a monitoring lead 410 containing electrodes 411–412 which are used to pick-up and carry the biological signals to the amplifier/filter 406.

The mission of the monitor and diagnostic system shown in FIG. 6 is to monitor and record, in a non-volatile memory 414, specific biological signals and events occurring adjacent to the monitoring electrodes 411–412. Later, at a convenient time, these recordings can be telemetered to the transmitter 12 which will produce, via a graphic recorder 416, a hard copy of the biological signals for the physician's examination and eventual diagnosis. Any time biological signals occur, they are scrutinized by the micro controller 46 for specific morphology which would cause the event to be stored into the memory 27 for later examination by the physician. An example of a typical use, would be to record dysfunctional endocardiac signals which, when inspected by a trained physician, may reveal the origin of a cardiac dysfunction not detected by conventional means, such as a surface EKG.

From the foregoing description, it will be apparent that the RF coupled, implantable medical system 10 with the rechargeable back-up power supply/source 44 of the present invention has a number of advantages, some of which have been described above and others of which are inherent in the invention. Also it will be understood that modifications can be made to the RF coupled, implantable medical system including the rechargeable back-up power supply/source 44 described above without departing from the teachings of the present invention. Accordingly, the scope of the invention is only to be limited as necessitated by the accompanying claims.

We claim:

1. An RF coupled implantable medical system comprising:

a transmitting unit;

a receiving unit including an implantable, electrically operated, medical device, RF energy receiving means, RF signal transmitting means and a rechargeable battery;

said transmitting unit including a power source, RF energy transmitting means, RF signal receiving means and first control means coupled to said RF energy transmitting means and to said RF signal receiving means for controlling the amount of RF energy transmitted to said receiving unit thereby to conserve on the amount of power obtained from said power source;

second control means coupled to said RF energy receiving means, to said rechargeable battery, to said RF signal transmitting means and to said implantable medical device, for adjusting the charging current flowing into said rechargeable battery, as a function of (a) the charge level of said rechargeable battery, (b) selected charging rate, and (c) selected power supply for the implantable medical device.

2. The system of claim 1 wherein said receiving unit includes a titanium housing enclosing said RF energy receiving means, said RF signal transmitting means, said rechargeable battery and said second control means.

3. The system of claim 1 wherein said RF energy transmitting means of said transmitting unit is constructed to transmit energy at a frequency as low as 10 Hz and up to at least 20,000 Hz.

4. The system of claim 1 wherein said rechargeable battery has a temperature sensor which is mounted closely adjacent thereto and which is coupled via said RF signal transmitting means to said first control means of said transmitting unit whereby the level of transmitted RF energy can be reduced proportionally to the reduction in charging rate of the rechargeable battery in said receiving unit, in order to reduce the power consumption from said power source powering said transmitting unit.

5. The system of claim 1 wherein said RF energy transmitting means of said transmitting unit includes mode selection means for recharging said rechargeable battery at a "fast" (high energy) rate or at a "trickle" (low to medium energy) rate.

6. The system of claim 1 wherein said transmitting unit includes power source selection means for setting said receiving unit to obtain its operating power from (1) RF coupled energy ("RF only" mode), (2) said rechargeable battery ("battery only" mode) or (3) automatically switch to "RF only" upon detection of said RF energy field, or "battery only" when said RF energy field is not detected ("combination" mode).

7. The system of claim 6 wherein said receiving unit includes: (a) means for rectifying said RF energy into a relatively high D.C. voltage, (b) means for regulating said high D.C. voltage into a lower D.C. voltage, and (c) means for detecting the presence of said RF energy field, said receiving unit, when set to operate in said "RF coupled energy" mode, is operable to supply regulated electrical energy to said implantable device so long as said transmitting unit is located proximate to said receiving unit and said receiving unit is sensing transmitted RF energy.

8. The system of claim 6 wherein said receiving unit, when said transmitting unit is set to operate in said "battery only" mode, is operable, periodically, to supply electrical energy to said implantable device from said rechargeable power supply for a period of at least 24 hours.

9. The system of claim 6 wherein said receiving unit, when set to operate in said "combination" mode, is operable to supply regulated D.C. electrical energy to said implantable device, so long as said transmitting unit is located proximate to said receiving unit and, separately, to "trickle charge" said rechargeable battery to maintain same fully charged.

10. The system of claim 1 wherein said first control means of said transmitting unit includes means for controlling the level of RF energy transfer from the transmitting unit to the receiving unit relative to one or more of one or more of the following parameters: (a) the charge level of said rechargeable battery, (b) selected charging rate, and (c) the selected power supply for said receiving unit.

11. The system of claim 1 wherein said receiving unit comprises means for measuring the charge level of said rechargeable battery and, upon sensing a fully charged battery, automatically up-links a coded signal which commands said transmitting unit to "stop" transmitting RF energy.

12. The system of claim 1 wherein said transmitting unit includes a visual display coupled to said first control means.

13. The system of claim 1 wherein said transmitting unit includes a keyboard coupled to said first control means.

14. The system of claim 13 wherein said keyboard includes keys to start and stop recharging of said rechargeable battery within the implantable medical device.

15. The system of claim 1 wherein said implanted medical device is a tissue stimulator.

16. The system of claim 1 wherein said implanted medical device is a drug delivery system.

17. The system of claim 1 wherein said implanted medical device is a cardiac pacemaker system.

18. The system of claim 1 wherein said implanted medical device is a cardioverter/defibrillator.

19. The system of claim 1 wherein said transmitting unit includes a battery, whereby said transmitting unit is portable and not dependant upon an a.c. power source.

20. The system of claim 19 wherein said battery can be a rechargeable battery or a non-rechargeable battery.

21. The system of claim 1 wherein said RF energy transmitting means of said transmitting unit includes mode selection means for setting said transmitting unit to operate in one of the following modes: "RF only", "battery only" or a "combination of both".

22. The system of claim 21 wherein said RF energy transmitting means of said transmitting unit controls the amount of RF energy transmitted and, (a) when said implanted receiving unit is set to operate in said "RF only" mode, said transmitted RF energy is automatically adjusted to the amount of RF energy required (i) to operate said implanted device and (ii) to maintain said rechargeable battery, which is powering said implanted device, in a fully charged state;

(b) when said implanted receiving unit is set to operate in said "battery only" mode, said transmitted RF energy is automatically adjusted to the amount of RF energy required (i) to operate said implanted device and (ii) to recharge quickly said rechargeable battery which is powering said implanted device; and, (c) when said implanted receiving unit is set to operate in said "combination of both" mode, said receiving unit is set to switch automatically to either said "RF only" mode upon detecting said transmitted RF energy, or to said "battery only" mode upon detecting a loss of said transmitted RF energy.

23. An RF coupled implantable medical system comprising:

a transmitting unit;

a receiving unit including an implantable, electrically operated, medical device;

said transmitting unit including RF energy transmitting means, RF signal receiving means and first control means coupled to said RF energy transmitting means and to said RF signal receiving means for controlling the amount of RF energy transmitted to said receiving unit;

said receiving unit including RF energy receiving means, RF signal transmitting means, a rechargeable power supply coupled to said RF energy receiving means and second control means for adjusting the charging current flowing into said rechargeable battery coupled to said rechargeable power supply means, to said RF energy receiving means, to said RF signal transmitting means and to said implanted medical device, and mode selection means for setting said receiving unit to operate in one of the following modes: (1) "RF only", (2) "battery only" or (3) "combination of both".

24. The system of claim 23 wherein said receiving unit, when said transmitting unit is set to operate in said "RF only" mode, is operable to supply electrical energy to said implantable device, so long as said transmitting unit is located proximate to said receiving unit and said receiving unit is sensing transmitted RF energy.

25. The system of claim 23 wherein said receiving unit, when said transmitting unit is set to operate in said "battery only" mode, is operable, periodically, to supply electrical energy to said implantable device from said rechargeable power supply for a period of at least 7 days.

26. The system of claim 23 wherein said receiving unit, when said transmitting unit is set to operate in said "battery only" mode, is operable, periodically, to supply electrical energy to said implantable device from said rechargeable power supply for a period of at least 24 hours.

27. The system of claim 23 wherein said receiving unit, when said transmitting unit is set to operate in said "combination" mode, is operable to supply electrical energy to said implantable device through a rectifier directly to said implanted medical device, so long as said transmitting unit is located proximate to said receiving unit, and, separately, to "trickle charge" said rechargeable power supply.

28. An RF coupled implantable medical system comprising:

a transmitting unit;

a receiving unit including an implantable, electrically operated, medical device;

said transmitting unit including RF energy transmitting means, RF signal receiving means and first control means coupled to said RF energy transmitting means and to said RF signal receiving means for controlling the amount of RF energy transmitted to said receiving unit;

said receiving unit including RF energy receiving means, RF signal transmitting means, a rechargeable power supply coupled to said RF energy receiving means and second control means for adjusting the charging current flowing into said rechargeable battery coupled to said rechargeable power supply means, to said RF energy receiving means, to said RF signal transmitting means and to said implanted medical device; and, said receiving unit comprising means for measuring the charge level of said rechargeable battery and, upon sensing a fully charged battery, automatically up-linking a coded signal which commands said transmitting unit to "stop" transmitting RF energy.

* * * * *